United States Patent [19]

Kaslow et al.

[11] Patent Number: 5,527,700
[45] Date of Patent: Jun. 18, 1996

[54] TARGET ANTIGENS OF TRANSMISSION BLOCKING ANTIBODIES FOR MALARIA PARASITES

[75] Inventors: David C. Kaslow, Kensington; Patrick E. Duffy, Bethesda, both of Md.

[73] Assignee: The United States of America as represented by the Department of Health and Human Services, Washington, D.C.

[21] Appl. No.: 126,593

[22] Filed: Sep. 22, 1993

Related U.S. Application Data

[63] Continuation-in-part of Ser. No. 912,294, Jul. 10, 1992, abandoned.

[51] Int. Cl.$^6$ .............................. C12N 15/30; C12N 1/21; C12N 1/19; C12N 5/10
[52] U.S. Cl. ................ 435/240.2; 536/23.7; 435/320.1; 435/252.3; 435/254.2; 435/69.3; 935/12; 935/65
[58] Field of Search ................ 435/69.3, 91, 172.3, 435/240.2, 252.3, 320.1, 235.1, 254.2; 536/237.1, 23.7; 530/350; 935/9, 29, 41, 56, 65, 73, 12

[56] References Cited

U.S. PATENT DOCUMENTS

| | | | |
|---|---|---|---|
| 4,546,082 | 10/1985 | Kurjan et al. | 435/172.3 |
| 4,707,445 | 11/1987 | McCutchan et al. | 435/91 |
| 4,769,330 | 9/1988 | Paoletti et al. | 435/172.3 |

FOREIGN PATENT DOCUMENTS

WO89/10936  11/1989  WIPO.
WO94/01552  1/1994  WIPO.

OTHER PUBLICATIONS

Wizel, Benjamin, et al. (1991) "Identication of a continuous and cross–reacting epitope for *Plasmodium falciparum* transmission–blocking immunity", *Proc. Natl. Acad. Sci. USA*, 88:9533–9537.

Elliot, John Francis, et al. (1990) "Genes for *Plasmodium falciparum* surface antigens cloned by expression in COS cells", *Proc. Natl. Acad. Sci USA*, 87:6363–6367.

Grotendorst, Cynthia A., et al. (1984) "A Surface Protein Expressed During Transformation of Zygotes of *Plasmodium gallinaceum* is a Traget of Transmission–Blocking Antibodies", *Infection and Immunity*, 45(3):775–777.

Duffy, Patrick E., et al. (1993) "p. 28 Belongs to a Family of Epidermal Growth Factor–like Antigens That Are Targets of Malaria Transmission–blocking Antibodies", *The Journal of Experimental Medicine*, 177:505–519.

Koslow Immunol. Lett. vol. 25 pp. 83–86 (1990).

Dane et al Science vol. 225 pp. 593–599 (1984).

Kaslow et al Nature vol. 333 pp. 74–76 (1988).

*Primary Examiner*—Mary E. Mosher
*Attorney, Agent, or Firm*—Townsend and Townsend and Crew

[57] ABSTRACT

The present invention relates novel methods and compositions for blocking transmission of *Plasmodium spp.* which cause malaria. In particular, P28 proteins are disclosed which, when administered to a susceptible organism, induce an immune response against a 28 kD protein on the surface of Plasmodium ookinetes and block transmission of malaria.

3 Claims, No Drawings

5,527,700

TARGET ANTIGENS OF TRANSMISSION BLOCKING ANTIBODIES FOR MALARIA PARASITES

This application is a continuation-in-part of Ser. No. 07/912,294, filed Jul. 10, 1992, now abandoned, which is incorporated herein by reference.

BACKGROUND OF THE INVENTION

Malaria continues to exact a heavy toll from mankind. Between 200 million to 400 million people are infected by *Plasmodium falciparum*, the deadliest of the malarial protozoans, each year. One to four million of these people die. Approximately 25 percent of all deaths of children in rural Africa between the ages of one and four years are caused by malaria.

The life cycle of the malaria parasite is complex. Infection in man begins when young malarial parasites or "sporozoites" are injected into the bloodstream of a human by a mosquito. After injection the parasite localizes in liver cells. Approximately one week after injection, the parasites or "merozoites" are released into the bloodstream to begin the "erythrocytic" phase. Each parasite enters a red blood cell in order to grow and develop. When the merozoite matures in the red blood cell, it is known as a trophozoite and, when fully developed, as a schizont. A schizont is the stage when nuclear division occurs to form individual merozoites which are released to invade other red cells. After several schizogonic cycles, some parasites, instead of becoming schizonts through asexual reproduction, develop into large uninucleate parasites. These parasites undergo sexual development.

Sexual development of the malaria parasites involves the female or "macrogametocyte" and the male parasite or "microgametocyte." These gametocytes do not undergo any further development in man. Upon ingestion of the gametocytes into the mosquito, the complicated sexual cycle begins in the midgut of the mosquito. The red blood cells disintegrate in the midgut of the mosquito after 10 to 20 minutes. The microgametocyte continues to develop through exflagellation and releases 8 highly flagellated microgametes. Fertilization occurs with the fusion of the microgamete and a macrogamete. The fertilized parasite, which is known as a zygote, then develops into an "ookinete." The ookinete penetrates the midgut wall of the mosquito and develops into an oocyst, within which many small sporozoites form. When the oocyst ruptures, the sporozoites migrate to the salivary gland of the mosquito via the hemolymph. Once in the saliva of the mosquito, the parasite can be injected into a host, repeating the life cycle.

Malaria vaccines are needed against different stages in the parasite's life cycle, including the sporozoite, asexual erythrocyte, and sexual stages. Each vaccine against a particular life cycle stage increases the opportunity to control malaria in the many diverse settings in which the disease occurs. For example, sporozoite vaccines would fight infection immediately after injection of the parasite into the host by the mosquito. First generation vaccines of this type have been tested in humans. Asexual erythrocytic stage vaccines would be useful in reducing the severity of the disease. Multiple candidate antigens for this stage have been cloned and tested in animals and in humans.

However, as drug-resistant parasite strains render chemoprophylaxis increasingly ineffective, a great need exists for a transmission-blocking vaccine. Such a vaccine would block the portion of the parasite's life cycle that takes place in the mosquito or other arthropod vector, thus preventing even the initial infection of humans. Several surface antigens serially appear on the parasite as it develops from gametocyte to gamete to zygote to ookinete within the arthropod midgut (Rener et al., *J. Exp. Med.* 158: 976–981, 1983; Vermeulen et al., *J. Exp. Med.* 162: 1460–1476, 1985). Several of these antigens induce transmission-blocking antibodies, but each antigen has demonstrated shortcomings: either a failure to generate an immune response in a broad segment of the vaccinated population (Good et al., *Science* 242:574–577, 1988; Graves et al., *Parasite Immunol.* 10: 209–218, 1988; Graves et al., *Infect. Immun.* 56:2818–2821, 1988; Carter et al., *J. Exp. Med.* 169:135–147, 1989). For example, monoclonal antibodies against a *P. falciparum* 25 kD a sexual stage surface protein, Pfs25, which is expressed on zygotes and ookinetes, partially block transmission of the parasite (Vermeulen et al., supra). However, partial blocking is not sufficient to arrest the spread of malaria.

The present invention fills the need for a means to completely block transmission of malaria parasites. The vaccine of the invention meets the requirements for a vaccine for controlling endemic malaria in developing countries: it induces high, long-lasting antibody titers, and can be produced in large amounts, at the lowest possible cost.

SUMMARY OF THE INVENTION

The present invention relates to methods for preventing transmission of malaria. In particular, the invention relates to methods for eliciting an immune response against parasites responsible for the disease. These methods comprise administering to a susceptible organism a pharmaceutical composition comprising a Pfs28 polypeptide in an amount sufficient to induce a transmission-blocking immune response.

The invention also relates to methods of preventing transmission of malaria comprising administering to a susceptible organism a pharmaceutical composition comprising a recombinant virus encoding a Pfs28 polypeptide in an amount sufficient to block transmission of the disease.

The invention further relates to pharmaceutical compositions comprising a pharmaceutically acceptable carrier and the Pfs28 polypeptides described above.

The invention also relates to isolated nucleic acids comprising nucleotide sequences encoding P28 proteins such as Pgs28 and Pfs28 polypeptides. These nucleic acids may be isolated from, for instance, *P. gallinaceum* or *P. falciparum*. The sequences are typically contained in an expression vector for recombinant expression of the proteins. The sequences can also be incorporated into recombinant viruses for use as vaccines or for recombinant expression of the proteins. Cell lines containing a nucleic acid encoding the immunogenic polypeptides in an expression vector are also disclosed.

DEFINITIONS

The term "P28" refers to 28 kD proteins expressed on the surface Plasmodium ookinetes. Examples of such proteins include Pgs28 and Pfs28 from *P. gallinaceum* and *P. falciparum*, respectively. The term encompasses native proteins as well as recombinantly produced modified proteins that induce a transmission blocking immune response. It also includes immunologically active fragments of these proteins.

In the expression of transgenes one of skill will recognize that the inserted polynucleotide sequence need not be identical and may be "substantially identical" to a sequence of the gene from which it was derived. As explained below, these variants are specifically covered by the terms Pfs28 and Pgs28.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the above term. In addition, the term "polynucleotide sequence from a Pfs28 gene" specifically includes those full length sequences substantially identical (determined as described below) with a Pfs28 gene sequence and that encode proteins that retain the function of the Pfs28 protein. Thus, in the case of the Pfs28 gene disclosed here, the above term includes variant polynucleotide sequences which have substantial identity with the sequences disclosed here and which encode proteins capable of inducing transmission blocking immune response.

The Pfs28 polypeptides of the present invention can consist of a full length Pfs28 protein, or a fragment thereof. Typically Pfs28 polypeptides are characterized by their ability to induce transmission blocking immune responses.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing sequences of the two sequences over a "comparison window" to identify and compare local regions of sequence similarity. A "comparison window" as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85: 2444 (1988), by computerized implementations of these algorithms. These references are incorporated herein by reference.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 70% sequence identity, preferably at least 80%, more preferably at least 90% and most preferably at least 95%, compared to a reference sequence using the programs described above using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 70%, preferably at least 80%, more preferably at least 90%, and most preferably at least 95%.

Another indication that nucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C.

Another indication that protein sequences are substantially identical is if one protein is immunologically reactive with antibodies raised against the other protein. Thus, the proteins of the invention include proteins immunologically reactive with antibodies raised against Pfs28 polypeptides.

A "susceptible organism" is a Plasmodium host that is susceptible to malaria, for example, humans and chickens. The particular susceptible organism or host will depend upon the Plasmodium species.

The phrases "biologically pure" or "isolated" refer to material which is substantially or essentially free from components which normally accompany it as found in its native state. Thus, the isolated P28 proteins of this invention do not contain materials normally associated with their in situ environment. Even where a protein has been isolated to a homogenous or dominant band, there are trace contaminants in the range of 5–10% of native protein which co-purify with the desired protein. Biologically pure material does not contain such endogenous co-purified protein.

DESCRIPTION OF THE PREFERRED EMBODIMENT

The present invention relates to novel compositions and methods for blocking transmission of parasites responsible for malaria. The invention provides agents capable of inhibiting the life cycle of the disease-causing parasite in the mosquito midgut. The agents include Pfs28 polypeptides that are useful for inducing antibodies that block transmission of the parasite, genes encoding such polypeptides, antibodies against these polypeptides, and compositions that are useful as vaccines against malaria.

The compositions of the invention can be used to block transmission of a number of parasites associated with malaria. Examples of parasites whose transmission may be blocked include the causative agents for malaria. Four species of the genus Plasmodium infect humans, *P. vivax, P. ovale, P. malariae,* and *P. falciparum*. In addition other Plasmodium species infect other animals. For instance, *P. gallinaceum* is responsible for avian malaria.

P28 Polypeptides

The present invention includes immunogenic polypeptides such as P28 proteins and fragments derived from the proteins that are useful for inducing an immune response when the proteins are injected into a human or other host animal. The antibodies that arise from the immune response block transmission of the parasite by interfering with the portion of the parasite's life cycle that occurs in the mosquito. For example, purified polypeptides having an amino acid sequence substantially identical to a subsequence of Pgs28 or Pfs28 may be used. Pgs28 is a *P. gallinaceum* surface protein of $M_r$ 28,000 kD (under reducing conditions) which is immunoprecipitated from an extract of zygotes/ookinetes by monoclonal antibodies that suppress but do not block malaria transmission (Grotendorst et al., *Infect. Immun.* 45:775–777, 1984). A gene encoding the protein is provided as SEQ ID NO: 1. The encoded protein is SEQ ID NO: 2.

Pfs28 is a homolog of Pgs28 from *P. falciparum*. The isolation of this gene is described in detail below. SEQ ID NO: 3 is a polynucleotide sequence encoding the protein. The encoded protein is SEQ ID NO: 4.

Pgs28 is similar in structure to both Pgs25 and Pfs25: all three proteins comprise a putative secretory signal sequence, followed by four EGF-like domains and a terminal hydrophobic transmembrane region without a cytoplasmic tail. Although the three proteins share the six-cysteine motif of the EGF-like domains, the functions of these proteins may be very different. EGF-like domains have been recognized in a range of proteins that have diverse functions (Davis, *New Biol.* 2:410–419, 1990).

Although Pgs28 and Pgs25 are structurally similar, they can be differentiated by their apparent $M_r$ on SDS-PAGE (28 kD for Pgs28, 25 kD for Pgs25), as well as their specific recognition by monoclonal antibodies (Grotendorst et al., supra.). For example, Pgs28 is recognized by the monoclonal antibody IID2B3B3, while Pgs25 is not. Similarly, the monoclonal antibody IID2-C5I recognizes Pgs25 but not Pgs28.

Included among the polypeptides of the present invention are proteins that are homologs of Pgs28 and Pfs28. Such homologs, also referred to as Pgs28 polypeptides or Pfs28 polypeptides, include variants of the native proteins constructed by in vitro techniques, and P28 proteins from parasites related to *P. gallinaceum* or *P. falciparum* that are homologous in features such as structure and relative time of expression in the parasite life cycle. One skilled in the art will appreciate, however, that for certain uses it would be advantageous to produce a Pgs28 or Pfs28 polypeptide that is lacking one of the structural characteristics; for example, one may remove the transmembrane domain to obtain a polypeptide that is more soluble in aqueous solution.

The P28 proteins of the invention may be purified from parasites isolated from infected host organisms. Methods for purifying desired proteins are well known in the art and are not presented in detail here. For a review of standard techniques see, *Methods in Enzymology*, "Guide to Protein Purification", M. Deutscher, ed. Vol. 182 (1990), which is incorporated herein by reference. For instance, Pfs28, Pgs28 or their homologous polypeptides can be purified using affinity chromatography, SDS-PAGE, and the like. For example, see Example 1 for a procedure for purifying Pgs28.

Nucleic Acids

Another aspect of the present invention relates to the cloning and recombinant expression of P28 proteins such as Pfs28 and Pgs28 obtained from the parasites discussed above. The recombinantly expressed proteins can be used in a number of ways. For instance, they can be used as transmission-blocking vaccines or to raise antibodies, as described below. In addition, oligonucleotides from the cloned genes can be used as probes to identify homologous polypeptides in other species.

Thus, the invention relies on routine techniques in the field of recombinant genetics, well known to those of ordinary skill in the art. A basic text disclosing the general methods of use in this invention is Sambrook et al., *Molecular Cloning, A Laboratory Manual*, Cold Spring Harbor Publish., Cold Spring Harbor, N.Y. 2nd ed. (1989).

In summary, the manipulations necessary to prepare nucleic acid segments encoding the polypeptides and introduce them into appropriate host cells involve 1) purifying the polypeptide from the appropriate sources, 2) preparing degenerate oligonucleotide probes corresponding to a portion of the amino acid sequence of the purified proteins, 3) screening a cDNA or genomic library for the sequences which hybridize to the probes, 4) constructing vectors comprising the sequences linked to a promoter and other sequences necessary for expression and 5) inserting the vectors into suitable host cells or viruses.

After isolation of the desired protein as described above, the amino acid sequence of the N-terminus is determined and degenerate oligonucleotide probes, designed to hybridize to the desired gene, are synthesized. Amino acid sequencing is performed and oligonucleotide probes are synthesized according to standard techniques as described, for instance, in Sambrook et al., supra.

Oligonucleotide probes useful for identification of desired genes can also be prepared from conserved regions of related genes in other species. For instance, probes derived from a gene encoding Pgs28 from *P. gallinaceum* or Pfs28 from *P. falciparum* may be used to screen libraries for homologous genes from other parasites of interest.

Genomic or cDNA libraries are prepared according to standard techniques as described, for instance, in Sambrook, supra. To construct genomic libraries, large segments of genomic DNA are generated by random fragmentation and are ligated with vector DNA to form concatemers that can be packaged into the appropriate vector. Two kinds of vectors are commonly used for this purpose, bacteriophage lambda vectors and plasmids.

To prepare cDNA, mRNA from the parasite of interest is first isolated. Eukaryotic mRNA has at its 3' end a string of adenine nucleotide residues known as the poly-A tail. Short chains of oligo d-T nucleotides are then hybridized with the poly-A tails and serve as a primer for the enzyme, reverse transcriptase. This enzyme uses RNA as a template to synthesize a complementary DNA (cDNA) strand. A second DNA strand is then synthesized using the first cDNA strand as a template. Linkers are added to the double-stranded cDNA for insertion into a plasmid or phage vector for propagation in *E. coli*.

Identification of clones in either genomic or cDNA libraries harboring the desired nucleic acid segments is performed by either nucleic acid hybridization or immunological detection of the encoded protein, if an expression vector is used. The bacterial colonies are then replica plated on solid support, such as nitrocellulose filters. The cells are lysed and probed with either oligonucleotide probes described above or with antibodies to the desired protein. For example, see Example 3 below, which describes the cloning of Pgs28, and Example 4, which describes cloning of Pfs28.

Other methods well known to those skilled in the art can also be used to identify desired genes. For example, the presence of restriction fragment length polymorphisms (RFLP) between wild type and mutant strains lacking a Pgs28 or Pfs28 polypeptide can be used. Amplification techniques, such as the polymerase chain reaction (PCR) can be used to amplify the desired nucleotide sequence. U.S. Pat. Nos. 4,683,195 and 4,683,202 describe this method. Sequences amplified by PCR can be purified from agarose gels and cloned into an appropriate vector according to standard techniques.

Standard transfection methods are used to produce prokaryotic, mammalian, yeast or insect cell lines which express large quantities of the Pgs28 or Pfs28 polypeptide, which is then purified using standard techniques. See, e.g., Colley et al., *J. Biol. Chem.* 264:17619–17622, 1989; and Guide to Protein Purification, supra.

The nucleotide sequences used to transfect the host cells can be modified according to standard techniques to yield Pfs 28 or Pgs28 polypeptides or fragments thereof, with a variety of desired properties. The polypeptides of the present invention can be readily designed and manufactured utilizing various recombinant DNA techniques well known to those skilled in the art. For example, the polypeptides can vary from the naturally-occurring sequence at the primary structure level by amino acid, insertions, substitutions, deletions, and the like. These modifications can be used in a number of combinations to produce the final modified protein chain.

The amino acid sequence variants can be prepared with various objectives in mind, including facilitating purification and preparation of the recombinant polypeptide. The modified polypeptides are also useful for modifying plasma half life, improving therapeutic efficacy, and lessening the severity or occurrence of side effects during therapeutic use. The amino acid sequence variants are usually predetermined variants not found in nature but exhibit the same immunogenic activity as naturally occurring Pgs28, Pfs28, or other P28 proteins. For instance, polypeptide fragments comprising only a portion (usually at least about 60–80%, typically 90–95%) of the primary structure may be produced. For use as vaccines, polypeptide fragments are typically preferred so long as at least one epitope capable of eliciting transmission blocking antibodies remains.

In general, modifications of the sequences encoding the homologous polypeptides may be readily accomplished by a variety of well-known techniques, such as site-directed mutagenesis (see, Gillman and Smith, *Gene* 8:81–97, 1979) and Roberts, S. et al., *Nature* 328:731–734, 1987). One of ordinary skill will appreciate that the effect of many mutations is difficult to predict. Thus, most modifications are evaluated by routine screening in a suitable assay for the desired characteristic. For instance, the effect of various modifications on the ability of the polypeptide to elicit transmission blocking can be easily determined using the mosquito feeding assays, described below. In addition, changes in the immunological character of the polypeptide can be detected by an appropriate competitive binding assay. Modifications of other properties such as redox or thermal stability, hydrophobicity, susceptibility to proteolysis, or the tendency to aggregate are all assayed according to standard techniques.

The particular procedure used to introduce the genetic material into the host cell for expression of the Pfs28 or Pgs28 polypeptide is not particularly critical. Any of the well known procedures for introducing foreign nucleotide sequences into host cells may be used. These include the use of calcium phosphate transfection, spheroplasts, electroporation, liposomes, microinjection, plasma vectors, viral vectors and any of the other well known methods for introducing cloned genomic DNA, cDNA, synthetic DNA or other foreign genetic material into a host cell (see Sambrook et al., supra). It is only necessary that the particular procedure utilized be capable of successfully introducing at least one gene into the host cell which is capable of expressing the gene.

The particular vector used to transport the genetic information into the cell is also not particularly critical. Any of the conventional vectors used for expression of recombinant proteins in prokaryotic and eukaryotic cells may be used. Expression vectors for mammalian cells typically contain regulatory elements from eukaryotic viruses. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG pAV009/A$^+$, pMTO10/A$^+$, pMAMneo-5, bacculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

The expression vector typically contains a transcription unit or expression cassette that contains all the elements required for the expression of the Pgs28 or Pfs28 polypeptide DNA in the host cells. A typical expression cassette contains a promoter operably linked to the DNA sequence encoding a Pgs28 or Pfs28 polypeptide and signals required for efficient polyadenylation of the transcript. The term "operably linked" as used herein refers to linkage of a promoter upstream from a DNA sequence such that the promoter mediates transcription of the DNA sequence. The promoter is preferably positioned about the same distance from the heterologous transcription start site as it is from the transcription start site in its natural setting. As is known in the art, however, some variation in this distance can be accommodated without loss of promoter function.

The DNA sequence encoding the Pfs28 or Pgs28 polypeptide will typically be linked to a cleavable signal peptide sequence to promote secretion of the encoded protein by the transformed cell. Additional elements of the cassette may include selectable markers, enhancers and, if genomic DNA is used as the structural gene, introns with functional splice donor and acceptor sites.

Enhancer elements can stimulate transcription up to 1,000 fold from linked homologous or heterologous promoters. Enhancers are active when placed downstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long term repeat from various retroviruses such as murine leukemia virus, murine or Rous sarcoma virus and HIV. See, *Enhancers and Eukaryotic Expression,* Cold Spring Harbor Pres, Cold Spring Harbor, N.Y. 1983, which is incorporated herein by reference.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Two distinct sequence elements are required for accurate and efficient polyadenylation: GU or U rich sequences located downstream from the polyadenylation site and a highly conserved sequence of six nucleotides, AAUAAA, located 11–30 nucleotides upstream. Termination and polyadenylation signals that are suitable for the present invention include those derived from SV40, or a partial genomic copy of a gene already resident on the expression vector.

Efficient expression and secretion in yeast is conveniently obtained using expression vectors based on those disclosed in Barr et al., *J. Biol. Chem.* 263: 16471–16478, 1988, or U.S. Pat. No. 4,546,082, which are incorporated herein by reference. In these vectors the desired sequences are linked to sequences encoding the yeast α-factor pheromone secretory signal/leader sequence. Suitable promoters to use include the ADH2/GAPDH hybrid promoter as described in Cousens et al., *Gene* 61:265–275 (1987), which is incorporated herein by reference. Yeast cell lines suitable for the present invention include BJ 2168 (Berkeley Yeast Stock Center) as well as other commonly available lines.

Any of a number of other well known cells and cell lines can be used to express the polypeptides of the invention. For instance, prokaryotic cells such as *E. coli* can be used. Eukaryotic cells include, Chinese hamster ovary (CHO) cells, COS cells, mouse L cells, mouse A9 cells, baby hamster kidney cells, C127 cells, PC8 cells, and insect cells.

Following the growth of the recombinant cells and expression of the Pfs28 or Pgs28 polypeptide, the culture medium is harvested for purification of the secreted protein. The media are typically clarified by centrifugation or filtration to remove cells and cell debris and the proteins are concentrated by adsorption to any suitable resin such as, for example, CDP-Sepharose, Asialoprothrombin-Sepharose 4B, or Q Sepharose, or by use of ammonium sulfate fractionation, polyethylene glycol precipitation, or by ultrafiltration. Other routine means known in the art may be equally suitable. Further purification of the Pgs28 polypeptide can be accomplished by standard techniques, for example, affinity chromatography, ion exchange chromatography, sizing chromatography or other protein purification techniques to obtain homogeneity. The purified proteins are then used to produce pharmaceutical compositions, as described below.

Transmission-blocking Antibodies

A further aspect of the invention includes antibodies against Pgs28, Pfs28, or their homologous polypeptides. The antibodies are useful for blocking transmission of parasites. Importantly, the antibodies of the invention are polyclonal and thus are capable of blocking parasite transmission, in contrast to monoclonal antibodies to Pgs28, which reduce but do not eliminate infectivity (Grotendorst et al., supra.).

Antibodies are typically tetramers of immunoglobulin polypeptides. As used herein, the term "antibody" refers to a protein consisting of one or more polypeptides substantially encoded by immunoglobulin genes. Immunoglobulin genes include those coding for the light chains, which may be of the kappa or lambda types, and those coding for the heavy chains. Heavy chain types are alpha, gamma, delta, epsilon and mu. The carboxy terminal portions of immunoglobulin heavy and light chains are constant regions, while the amino terminal portions are encoded by the myriad immunoglobulin variable region genes. The variable regions of an immunoglobulin are the portions that provide antigen recognition specificity. The immunoglobulins may exist in a variety of forms including, for example, Fv, Fab, and F(ab)$_2$, as well as in single chains (e.g., Huston et al., *Proc. Natl. Acad. Sci. U.S.A.*, 85:5879–5883 (1988) and Bird et al., *Science* 242: 423–426, 1988, both of which are incorporated herein by reference). (See, generally, Hood et al., *Immunology*, Benjamin, N.Y., 2nd ed. (1984), and Hunkapiller and Hood, *Nature,* 323: 15–16, 1986, which are incorporated herein by reference). Single-chain antibodies, in which genes for a heavy chain and a light chain are combined into a single coding sequence, may also be used.

Vaccines

The immunoglobulins, nucleic acids, and polypeptides of the present invention are also useful as prophylactics, or vaccines, for blocking transmission of malaria or other diseases caused by parasites. Compositions containing the immunoglobulins, polypeptides, or a cocktail thereof are administered to a subject, giving rise to an anti-Pgs28 or anti-Pfs28 polypeptide immune response in the mammal entailing the production of anti-Pgs28 or anti-Pfs28 polypeptide immunoglobulins. The Pgs28 or Pfs28 polypeptide-specific immunoglobulins then block transmission of the parasite from the subject to the arthropod vector, preventing the parasite from completing its life cycle. An amount of prophylactic composition sufficient to result in blocking of transmission is defined to be an "immunologically effective dose."

The isolated nucleic acid sequences coding for Pgs28, Pfs28, or their homologous polypeptides can also be used to transform viruses which transfect host cells in the susceptible organism. Live attenuated viruses, such as vaccinia or adenovirus, are convenient alternatives for vaccines because they are inexpensive to produce and are easily transported and administered. Vaccinia vectors and methods useful in immunization protocols are described in, e.g., U.S. Pat. No. 4,722,848, incorporated herein by reference.

Suitable viruses for use in the present invention include, but are not limited to, pox viruses, such as, canarypox and cowpox viruses, and vaccinia viruses, alpha viruses, adenoviruses, and other animal viruses. The recombinant viruses can be produced by methods well known in the art: for example, using homologous recombination or ligating two plasmids together. A recombinant canarypox or cowpox virus can be made, for example, by inserting the gene encoding the Pgs28, Pfs28, or other homologous polypeptide into a plasmid so that it is flanked with viral sequences on both sides. The gene is then inserted into the virus genome through homologous recombination.

A recombinant adenovirus virus can be produced, for example, by ligating two plasmids each containing 50% of the viral sequence and the DNA sequence encoding the Pgs28, Pfs28, or other homologous polypeptide. Recombinant RNA viruses such as the alpha virus can be made via a cDNA intermediate using methods known in the art.

The recombinant virus of the present invention can be used to induce anti-Pfs28 or anti-Pgs28 polypeptide antibodies in mammals, such as mice or humans. In addition, the recombinant virus can be used to produce the Pgs28 or Pfs28 polypeptides by infecting host cells which in turn express the polypeptide.

The present invention also relates to host cells infected with the recombinant virus of the present invention. The host cells of the present invention are preferably eukaryotic, such as yeast cells, or mammalian, such as BSC-1 cells. Host cells infected with the recombinant virus express the Pgs28 or Pfs28 polypeptides on their cell surfaces. In addition, membrane extracts of the infected cells induce transmission blocking antibodies when used to inoculate or boost previously inoculated mammals.

In the case of vaccinia virus (for example, strain WR), the sequence encoding the Pgs28 or Pfs28 polypeptides can be inserted into the viral genome by a number of methods including homologous recombination using a transfer vector, pTKgpt-OFIS as described in Kaslow et al., *Science* 252:1310–1313, 1991, which is incorporated herein by reference.

The Pfs28 or Pgs28 polypeptides, or recombinant viruses of the present invention can be used in pharmaceutical and vaccine compositions that are useful for administration to mammals, particularly humans, to block transmission of a variety of infectious diseases. The compositions are suitable for single administrations or a series of administrations. When given as a series, inoculations subsequent to the initial administration are given to boost the immune response and are typically referred to as booster inoculations.

The pharmaceutical compositions of the invention are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration that comprise a solution of the agents described above dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the polypeptides or recombinant viruses are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

In therapeutic applications, Pfs 28 or Pgs28 polypeptides or viruses of the invention are administered to a patient in an amount sufficient to prevent parasite development in the arthropod and thus block transmission of the disease. An amount adequate to accomplish this is defined as a "therapeutically effective dose." Amounts effective for this use will depend on, e.g., the particular polypeptide or virus, the manner of administration, the weight and general state of health of the patient, and the judgment of the prescribing physician.

The vaccines of the invention contain as an active ingredient an immunogenically effective amount of the Pgs28 or Pfs28 polypeptides or recombinant virus as described herein. Useful carriers are well known in the art, and include, e.g., thyroglobulin, albumins such as human serum albumin, tetanus toxoid, polyamino acids such as poly(D-lysine:D-glutamic acid), influenza, hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art.

Vaccine compositions containing the polypeptides or viruses of the invention are administered to a patient to elicit a transmission-blocking immune response against the antigen and thus prevent spread of the disease through the arthropod vector. Such an amount is defined as an "immunogenically effective dose." In this use, the precise amounts again depend on the patient's state of health and weight, the mode of administration, and the nature of the formulation.

The following examples are offered by way of illustration, not by way of limitation.

EXAMPLE 1

Localization of Pgs28

Methods

To label Pgs28, mature ookinetes were fixed for 30 min at 4° C. in 0.1% glutaraldehyde and 4% formaldehyde in phosphate-buffered saline (PBS). Parasites were then incubated with ascites containing mAb IID2-B3B3, an $IgG^1$ antibody. Ascites was diluted 1:20 in PBS with 1% BSA. After 5 washes with PBS/BSA, the cells were incubated with goat anti-mouse antibodies (EY Labs, Inc., San Mateo, Calif.) conjugated with colloidal gold (10–15 nm), then washed 3 times with PBS.

Ookinetes were post-fixed in 1% osmium tetroxide in 0.1M cacodylate buffer solution containing 2 mM $CaCl_2$ and 0.8% potassium ferricyanide, dehydrated in acetone, and embedded in Epon. Routine thin sections were stained with uranyl acetate and lead citrate, then visualized (post-fixing, embedding, and visualization by Dr. Paulo Pimenta, Laboratory of Parasitic Diseases, NIH, Bethesda, Md.).

Results

Immunoelectron microscopy, using mAb IID2 B3B3, demonstrated the uniform and extensive distribution of Pgs28 in both the longitudinal and presumed transverse sections of the mature ookinete. This corroborates earlier biosynthetic work that showed that Pgs25 achieves peak synthesis in the early hours after parasite fertilization, then is exceeded about 10 hours after fertilization by expression of Pgs28, which becomes the predominant surface protein of mature ookinetes (Kumar et al., *Mol. Biochem. Parasitol.* 14:127–139, 1985).

EXAMPLE 2

Purification of Pgs28

Methods

Ookinete antigens. Purified zygotes of *P. gallinaceum* were prepared from the parasitized blood of infected White Leghorn chickens as previously described (Kaushal et al., *J. Immunol.* 131:2557–2562, 1983). Zygotes were transformed in vitro into ookinetes by incubation ($1 \times 10^7$/ml) for 24 hr at 26° C. in Medium 199 with 17 mM dextrose, 1 mM L-glutamine, 100 U/ml penicillin, and 100 μg/ml streptomycin, pH 8.4. Morgan et al. *Proc. Soc. Exp. Biol. Med.* 73: (1950). Antigens were extracted with NETT buffer: 50 mM Tris, 150 mM NaCl, 5 mM EDTA, 0.5% Triton X-100, 0.02% $NAN_3$, pH 7.4.

Pgs28 Purification. Pgs28 was immunoaffinity-purified from ookinete extracts using monoclonal antibody IID2-B3B3 (Grotendorst et al., supra.) covalently linked to Sepharose 4B beads (mAb covalently attached to Protein A by bifunctional cross-linker) in a column, (protocol for column use in manufacturer's literature ImmunoPure® Kit, Pierce, Rockford Ill.). The resin with bound Pgs28 was suspended in electroelution buffer (50 mM$NH_4HCO_3$, 0.1% SDS), and Pgs28 electroeluted from the resin for 4 h at 10 mA. The sample containing Pgs28 was concentrated in a Speed Vac® dessicator or Amicon Centricon® 10 microconcentrater, diluted 1:1 with SDS-PAGE sample buffer (8% SDS, 3.0M Tris-HCl, pH 8.45, 24% glycerol, 0.015% Serva Blue G, and 0.005% Phenol Red), and size-fractionated by SDS-PAGE in a 10% polyacrylamide gel under nonreducing or reducing conditions. Pgs28 was electroblotted from the gel onto pure nitrocellulose, in situ digested with trypsin (Matsudaira, *J. Biol. Chem.* 262:10035–10038, 1987) and microsequenced (Bill Lane, Harvard MicroChemistry, Cambridge, Mass.) or electroblotted onto PVDF for N-terminal sequence (John Coligan, Biological Resources Branch, NIH, Bethesda, Md.).

Results

Immunoaffinity purification of Pgs28 from crude ookinete extract resulted in a dominant band of $M_r$ 34,000 on 10% SDS-PAGE, which was electroblotted onto polyvinylidene difluoride for N-terminal sequencing of the mature protein. βmercaptoethanol reduction of the immunoaffinity-purified material caused Pgs28 to comigrate on SDS-PAGE with the small amount of mouse light chain that co-eluted from the immunoaffinity column. After blotting onto nitrocellulose, the protein was digested with trypsin, and eluted peptides separated by reverse phase high pressure liquid chromatography. Three tryptic peptides were sequenced, of which two (called NT14 and NT16) were unique when screened in Swiss Prot (Release 17, Centre Medicale Universitaire, Geneva, Switzerland) and one was substantially identical to the mouse antibody light chain.

Pgs28 and Pgs25, in addition to having different molecular weights, can also be differentiated by their specific recognition by monoclonal antibodies (Grotendorst et al., supra.). By Western blot analysis (data not shown), Triton X-100 extracts of ookinetes depleted of Pgs28 by chromatography with mAb IID2-B3B3 (specific for Pgs28) were not depleted of Pgs25 as assayed by mAb IID2-C5I (specific for Pgs25). Furthermore, the immunoaffinity-purified Pgs28 was, by Western blot analysis, recognized by IID2 B3B3, but not by mAb IID2-C5I.

EXAMPLE 3

Cloning of Pgs28 Gene

Methods

Screening genomic DNA library. The amino acid sequences of peptides from tryptic digests of Pgs28 were used to derive synthetic degenerate oligonucleotide probes, which were synthesized on an Applied Biosystems Inc. automated synthesizer. A HindIII-digested genomic library of *P. gallinaceum* DNA was constructed in pUC13 and electroporated into *E. coli*. The colonies were screened with the probe NT14AGT (5'-TT (AG)TT (AG)TC (TC)TT GTA TGG (AG)TC (TC)TC-3') (SEQ ID NO: 5) by hybridizing at 45° C. for 16 h and washing the filters at a final stringency of 6×SSC (=1M sodium chloride, 0.1M sodium citrate, pH 7.0), 0.1% SDS at 49° C. for 5 m. Autoradiography at −70° C. for 4–16 h was performed to identify positive colonies. Using the probes, as well as other synthetic oligonucleotides as sequencing primers, the nucleotide sequence for positive colonies was determined by the dideoxynucleotide terminator method.

Results

Completely degenerate oligonucleotide probes based on the Pfs28 amino acid sequences obtained in Example 2 were used to probe total RNA from *P. gallinaceum* zygotes that had grown for six hours. The probes hybridized to a 1.4 Kb transcript. However, these probes failed to detect the gene by either Southern blot hybridization with genomic digests or colony screening of existing cDNA and genomic libraries. To increase specificity, the antisense oligonucleotide based on peptide NT14 was synthesized without degeneracy at positions 12 (either A or G used) and 15 (where each of the four nucleotides was used in separate constructs), then hybridized with a Northern blot of total RNA obtained from 6 hour old zygotes. A greatly enhanced signal occurred with guanosine at position 12 and thymidine at position 15. This probe (NT14AGT) identified a 3.3 kB band on Southern blot hybridization of a HindIII digest of *P. gallinaceum* genomic DNA, and subsequently identified a positive clone (clone 9A1) in a library of HindIII-digested genomic DNA ligated into pUC13.

Clone 9A1 was sequenced, and found to have a 666 bp open reading frame (SEQ ID NO: 1 and SEQ ID NO: 2). All three previously sequenced peptides were included in the resulting deduced amino acid sequence, the only misread occurring at position 8 of the N terminus (sequenced as proline; deduced as cysteine). The structural homology between Pgs28 and both Pgs25 and Pfs25 is considerable; all three proteins have a putative secretory signal sequence, then four EGF-like domains, and a terminal hydrophobic transmembrane region without a cytoplasmic tail. Although the 6 cysteine motif of the EGF-like domains is shared between these proteins, this does not suggest a shared function. These domains have been recognized in a range of proteins with a diversity of functions (Davis, *New Biol.* 2:410–419, 1990).

EXAMPLE 4

Cloning of Pfs28 Gene

The presence of Pfs28 was detected using sequences from Pgs28. The Pgs28 gene was amplified by polymerase chain reaction using primers that flank the open reading frame in clone 9A1. This fragment was radiolabelled and used to probe genomic DNA from asexual stage *P. falciparum*

(strain 3D7) or *P. gallinaceum* parasites. The DNA from the parasites was electrophoresed through 1% agarose gel and transferred to nylon. Filters were hybridized overnight at $T_m$10° C. with $^{32}$P-labelled probes, then washed with 6×SSC, 0.1% SDS at $T_m$–5° C. for 5 mins (Southern blots) or 7 mins (Northern blots). Autoradiographs were developed after 4–16 h exposure at –70° C.

When hybridized with restriction endonuclease-digested genomic DNA from *P. falciparum*, the Pgs28 probe hybridized to a unique band. The restriction digestion pattern was distinct from that seen with Pfs25 probes.

The Pfs28 gene was isolated as follows. Aligning the nucleotide sequences of Pgs28, Pgs25, Pfs25, and Pbs21, 3 areas of high homology were recognized. Completely degenerate oligonucleotide primers based on these sequences were synthesized. Two of these primers PfPCR28S1 (5'-GG(AT)T(AT)T(CT)TAAT (AT) (CG)AGATGAG-3') (SEQ ID NO: 6) and PfPCR28A1 (5'-ACT(AT)T(AG)CC(AT)ATA(AT) (AT)ACATG A(AG)CA-3') (SEQ ID NO: 7) were used to amplify an approximately 320-bp product from the genomic DNA of *P. falciparum* (strain 7G8) by the polymerase chain reaction. Digestion of this amplified product with Nsp7524I revealed bands consistent with Pfs25 as well as a distinct set of bands. Using primer PfPCR28A1, the Nsp7524I-digested PCR product was directly sequenced by the dideoxynucleotide terminator method. The deduced amino acid sequence was novel and contained an EGF-like motif.

Based on this novel sequence, a non-degenerate oligonucleotide primer Pfs28SL (5'-GCTTGTGAT-GAATACGCTTACTGTTTCGATTTAGG- 3') (SEQ ID NO: 8) was synthesized and used in conjunction with PfPCR28A1 to PCR-amplify a >200-bp product from strain 7G8 DNA. This product was $^{32}$P-labelled by extension from random primers, then used to probe a size-selected library of EcoRI/HindIII-digested genomic DNA (*P. falciparum* strain 7G8) inserted into vector pUC18. A clone with a 1.3 kB insert was obtained which contained a 430-nucleotide sequence encoding a cysteine-rich protein homologous to Pgs28; the clone lacked the 5'-terminal coding sequence.

Using two non-degenerate oligonucleotides Pfs28S2 (5'-GAGGACACGTGTGGAAAG-3') (SEQ ID NO: 9) and Pfs28SLA1 (5'-CCATACTTAACCACAATA- 3') (SEQ ID NO: 10) designed from the available sequence, a 270-bp product was PCR-amplified from strain 7G8 genomic DNA, $^{32}$P-labelled the product by random primer extension, then used to probe a size-selected library of EcoRI/NsiI-digested genomic DNA (strain 7G8) inserted into vector pUC18. Clone p6-1, which had a 1.7 kB insert containing the full length coding sequence for a Pfs28 protein was isolated.

Employing the dideoxynucleotide terminator method, the open reading frame was sequenced in its entirety in both directions, save the 5'-most 17 nucleotides which were only sequenced in the antisense direction. The 654-nucleotide open reading frame of Pfs28 encodes a cysteine-rich protein of 218 residues, whose primary structure comprises an initial signal sequence, followed by four EGF-like domains, then a terminal hydrophobic region without a cytoplasmic tail.

EXAMPLE 5

Blocking of *P. gallinaceum* Transmission

Immunizations. Pgs28 contained in polyacrylamide gel was dispersed in Ribi Adjuvant System (RAS) emulsion (MPL®+TDM) according to the manufacturer's protocol (Ribi ImmunoChem Research, Inc., Hamilton, Minn.). Male BALB/c mice, aged 4–6 weeks, were immunized intraperitoneally with 0.2 ml emulsion for primary immunization, and again at 3 and 6 weeks for boosting immunization. The control group of mice received polyacrylamide gel without antigen dispersed in adjuvant.

Transmission-blocking assays for malaria. The method of quantifying transmission-blocking antibodies in vitro was generally as described in Quakyi et al., *J. Immunol.* 139:4213, 1987, which is incorporated herein by reference. Briefly, mosquitoes were fed on *P. gellinaceum*-parasitized material (either infected blood or mature ookinetes mixed with naive blood) through a membrane. Infectivity was measured 1 week after feeding by counting the number of oocysts per mosquito midgut of 20 mosquitoes. By adding post-immunization mouse sera (diluted in heat-inactivated normal chicken serum) to the parasitized blood, we measured the effect of the sera on parasite transmission. If the addition of immune sera reduced infectivity compared with the control then the immune sera demonstrated transmission- blocking antibodies.

Statistical analysis. We analyzed two endpoints of transmission-blocking antibodies: the percentage of mosquitoes in a batch that had one or more oocysts on their midgut, and the number of oocysts per midgut. Mosquito batches fed on blood containing immune sera were compared with those fed on blood with control sera. The percentage of mosquitoes with oocysts was compared by Chi-square analysis. The number of oocysts/midgut was compared by Wilcoxon's rank sum analysis.

Results

Polyclonal, monospecific antisera from mice immunized with immunoaffinity-purified Pgs28 completely blocks *P. gallinaceum* transmission. Mosquitoes which received αPgs28 antisera in addition to parasitized chicken blood developed significantly fewer oocysts compared to those mosquitoes which received either pre-immune or control sera (Table 1 A,B, and C). In fact, in three transmission-blocking assays, 47 mosquitoes received αPgs28 antisera, of which only a single mosquito was infected, and in that mosquito only a single oocyst developed.

TABLE 1

Transmission-blocking activity of sera from immunized animals

| Sample | Mean oocyst number (range) | Infectivity percent of prebleed | Mosq. infected\ Mosq. dissected |
|---|---|---|---|
| A. | | | |
| Pre-immune | 39.2 (21–62) | 0% | 4/4 |
| Anti-Pgs 28 | 0(0) | | 0/5 |
| B. | | | |
| Control | 6.5 (0–30) | <0.01% | 17/22 |
| Anti-Pgs 28 | 0.04 (0–1) | | 1/23 |
| C. | | | |
| Control | 13.0 (5–26) | 0% | 6/6 |
| Anti-Pgs 28 | 0 (0) | | 0/20 |
| D. | | | |
| Control | 33.5 (0–302) | 12.5% | 17/20 |
| Anti-Pgs 28 | 4.2 (0–56) | | 7/21 |

Polyclonal antisera against Pgs28 impairs at least two distinct stages of parasite sexual development. During an overnight incubation in M199, *P. gallinaceum* zygotes readily transform into elongated ookinetes, reproducing the events which naturally occur in the mosquito midgut. The addition of αPgs28 antisera significantly reduced the proportion of parasites which underwent this in vitro transformation (Table 2). In vivo, the ookinete traverses the midgut epithelium, then lodges beneath the basal lamina to develop into an oocyst. This development can be accomplished by feeding mature ookinetes (grown in M199) to mosquitoes; however, the proportion of mosquitoes which develop oocysts was significantly reduced by adding αPgs28 antisera to in vitro ookinetes (Table 1D). As the incubation of mature ookinetes with αPgs28 antisera in vitro did not induce parasite death (data not shown), the explanation(s) for the antibody effects remains unclear.

TABLE 2

In vitro transformation-blocking activity of sera from immunized animals

| Sample | Number of Ookinetes | Total number of parasites | Percent Transformation |
|---|---|---|---|
| A. | | | |
| Control | 65 | 129 | 50.4% |
| Anti-Pgs 28 | 10 | 155 | 6.5% |
| B. | | | |
| Control | 55 | 143 | 38.5% |

TABLE 2-continued

In vitro transformation-blocking activity of sera from immunized animals

| Sample | Number of Ookinetes | Total number of parasites | Percent Transformation |
|---|---|---|---|
| Anti-Pgs 28 | 16 | 109 | 14.7% |
| C. | | | |
| Control | 36 | 101 | 35.6% |
| Anti-Pgs 28 | 5 | 104 | <1.0% |

Monoclonal antibodies to Pgs28 have previously been shown to suppress the number of oocysts that developed after an infectious bloodmeal, reducing infectivity (measured as mean number oocysts/midgut) to 38–48% of control (Grotendorst et al., supra.). The clear superiority of polyclonal antisera over the prior art monoclonal antibodies, as demonstrated herein, may represent the combined result of multiple blocks in parasite development.

The invention has been described in these examples and the above disclosure in some detail for the purposes of clarity and understanding. It will be apparent, however, that certain changes and modifications may be practiced within the scope of the appended claims.

What is claimed is:

1. An isolated nucleic acid comprising a sequence encoding the pfs28 polypeptide.

2. The nucleic acid of claim 1, wherein the nucleic acid is SEQ ID NO: 3.

3. A cell line transformed with a vector containing the nucleic acid of claim 1.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 858 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 123..791
        ( D ) OTHER INFORMATION: /product="Pgs28 surface protein
            from Plasmodium gallinaceum"

( x i ) SEQUENCE DESCRIPTION: SEQ ID NO:1:

```
TTTTTTGTCA  TATTATTATC  ATTTTTAAAT  TCATTTCTAT  TTCCCATAAT  AAATTATTCT      60

ACAAAATATT  CAAACGAAGA  TTATTTAGTA  AACGAAAACA  ATTTAACAT   TTATTTAAAA    120

AA ATG AAA ATT CCT AGT TTA TAT TTT TTC TTT TTT ATT CAA ATT GCA            167
   Met Lys Ile Pro Ser Leu Tyr Phe Phe Phe Phe Ile Gln Ile Ala
   1               5                   10                  15

ATA ATA TTA ACT ATT GCA GCT CCT TCA GAT GAT GAA CCT TGT AAA AAT          215
Ile Ile Leu Thr Ile Ala Ala Pro Ser Asp Asp Glu Pro Cys Lys Asn
                20              25                  30

GGT TAT TTA ATA GAG ATG AGC AAT CAT ATT GAG TGC AAA TGT AAT AAT          263
Gly Tyr Leu Ile Glu Met Ser Asn His Ile Glu Cys Lys Cys Asn Asn
            35                  40                  45

GAC TAT GTA TTA ACG AAT CGT TAT GAG TGT GAA CCA AAA AAT AAA TGT          311
Asp Tyr Val Leu Thr Asn Arg Tyr Glu Cys Glu Pro Lys Asn Lys Cys
        50                  55                  60
```

| | | | | | | | | | | | | | | | | |
|---|---|---|---|---|---|---|---|---|---|---|---|---|---|---|---|---|
|ACA|AGT|TTA|GAA|GAT|ACA|AAT|AAA|CCT|TGT|GCT|GAC|TAT|GCT|AGA|TGT|359|
|Thr|Ser|Leu|Glu|Asp|Thr|Asn|Lys|Pro|Cys|Ala|Asp|Tyr|Ala|Arg|Cys| |
| |65| | | |70| | | |75| | | | | | | |

| | | | | | | | | | | | | | | | | |
|---|---|---|---|---|---|---|---|---|---|---|---|---|---|---|---|---|
|CTT|GAG|GAT|CCA|TAC|AAA|GAT|AAT|AAA|AGT|AAT|TTT|TAT|TGC|CTA|TGT|407|
|Leu|Glu|Asp|Pro|Tyr|Lys|Asp|Asn|Lys|Ser|Asn|Phe|Tyr|Cys|Leu|Cys| |
|80| | | | |85| | | |90| | | | | |95| |

| | | | | | | | | | | | | | | | | |
|---|---|---|---|---|---|---|---|---|---|---|---|---|---|---|---|---|
|AAT|AGA|GGT|TAT|ATT|CAA|TAT|GAA|GAT|AAA|TGT|ATT|CAA|GCG|GAA|TGT|455|
|Asn|Arg|Gly|Tyr|Ile|Gln|Tyr|Glu|Asp|Lys|Cys|Ile|Gln|Ala|Glu|Cys| |
| | | | |100| | | | |105| | | | |110| | |

| | | | | | | | | | | | | | | | | |
|---|---|---|---|---|---|---|---|---|---|---|---|---|---|---|---|---|
|AAT|TAT|AAG|GAA|TGT|GGA|GAA|GGA|AAA|TGT|GTA|TGG|GAT|GGA|ATA|CAT|503|
|Asn|Tyr|Lys|Glu|Cys|Gly|Glu|Gly|Lys|Cys|Val|Trp|Asp|Gly|Ile|His| |
| | |115| | | | |120| | | | |125| | | | |

| | | | | | | | | | | | | | | | | |
|---|---|---|---|---|---|---|---|---|---|---|---|---|---|---|---|---|
|GAG|GAT|GGT|GCA|TTT|TGT|TCA|TGT|AAT|ATT|GGT|AAA|GTC|ATA|AAT|CCA|551|
|Glu|Asp|Gly|Ala|Phe|Cys|Ser|Cys|Asn|Ile|Gly|Lys|Val|Ile|Asn|Pro| |
| | |130| | | | |135| | | | |140| | | | |

| | | | | | | | | | | | | | | | | |
|---|---|---|---|---|---|---|---|---|---|---|---|---|---|---|---|---|
|GAA|GAT|AAT|AAT|AAA|TGC|ACA|AAA|GAC|GGA|GAT|ACT|AAA|TGT|ACA|CTA|599|
|Glu|Asp|Asn|Asn|Lys|Cys|Thr|Lys|Asp|Gly|Asp|Thr|Lys|Cys|Thr|Leu| |
| |145| | | | |150| | | | |155| | | | | |

| | | | | | | | | | | | | | | | | |
|---|---|---|---|---|---|---|---|---|---|---|---|---|---|---|---|---|
|GAA|TGT|GCA|CAA|GGC|AAG|AAA|TGC|ATA|AAA|CAT|GAT|GTG|TAT|TAT|ATG|647|
|Glu|Cys|Ala|Gln|Gly|Lys|Lys|Cys|Ile|Lys|His|Asp|Val|Tyr|Tyr|Met| |
|160| | | | |165| | | | |170| | | | |175| |

| | | | | | | | | | | | | | | | | |
|---|---|---|---|---|---|---|---|---|---|---|---|---|---|---|---|---|
|TGT|GGT|AAT|GAT|AAT|TCT|GGG|TCT|GGG|TCT|GGT|GGT|GGT|GGT|GGT|GGT|695|
|Cys|Gly|Asn|Asp|Asn|Ser|Gly|Ser|Gly|Ser|Gly|Gly|Gly|Gly|Gly|Gly| |
| | | |180| | | | |185| | | | |190| | | |

| | | | | | | | | | | | | | | | | |
|---|---|---|---|---|---|---|---|---|---|---|---|---|---|---|---|---|
|GGT|AAC|AGC|CCA|CCT|CCT|AGC|AGT|GGT|AAT|AGC|ACC|TTA|TCC|CTT|TTC|743|
|Gly|Asn|Ser|Pro|Pro|Pro|Ser|Ser|Gly|Asn|Ser|Thr|Leu|Ser|Leu|Phe| |
| | | |195| | | | |200| | | | |205| | | |

| | | | | | | | | | | | | | | | | |
|---|---|---|---|---|---|---|---|---|---|---|---|---|---|---|---|---|
|AAT|GCA|TTA|AAT|ATA|GTT|TTC|TTA|ATA|GCT|GTA|ATT|TAT|ATC|ATT| |788|
|Asn|Ala|Leu|Asn|Ile|Val|Phe|Leu|Ile|Ala|Val|Ile|Tyr|Ile|Ile| | |
| | |210| | | | |215| | | | |220| | | | |

TAAATATATG GCTGCACTTA ATGAAAGTAA TATAATTACC AGACCAAATT AAATCATAAT 848

TATATGCACT 858

( 2 ) INFORMATION FOR SEQ ID NO:2:

( i ) SEQUENCE CHARACTERISTICS:
        ( A ) LENGTH: 222 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
|Met|Lys|Ile|Pro|Ser|Leu|Tyr|Phe|Phe|Phe|Phe|Ile|Gln|Ile|Ala|Ile|
|1| | | |5| | | | |10| | | | |15| |

| | | | | | | | | | | | | | | | |
|---|---|---|---|---|---|---|---|---|---|---|---|---|---|---|---|
|Ile|Leu|Thr|Ile|Ala|Ala|Pro|Ser|Asp|Glu|Pro|Cys|Lys|Asn|Gly|
| | | |20| | | | |25| | | | |30| | |

| | | | | | | | | | | | | | | | |
|---|---|---|---|---|---|---|---|---|---|---|---|---|---|---|---|
|Tyr|Leu|Ile|Glu|Met|Ser|Asn|His|Ile|Glu|Cys|Lys|Cys|Asn|Asn|Asp|
| | |35| | | | |40| | | | |45| | | |

| | | | | | | | | | | | | | | | |
|---|---|---|---|---|---|---|---|---|---|---|---|---|---|---|---|
|Tyr|Val|Leu|Thr|Asn|Arg|Tyr|Glu|Cys|Glu|Pro|Lys|Asn|Lys|Cys|Thr|
| |50| | | | |55| | | | |60| | | | |

| | | | | | | | | | | | | | | | |
|---|---|---|---|---|---|---|---|---|---|---|---|---|---|---|---|
|Ser|Leu|Glu|Asp|Thr|Asn|Lys|Pro|Cys|Ala|Asp|Tyr|Ala|Arg|Cys|Leu|
|65| | | | |70| | | | |75| | | | |80|

| | | | | | | | | | | | | | | | |
|---|---|---|---|---|---|---|---|---|---|---|---|---|---|---|---|
|Glu|Asp|Pro|Tyr|Lys|Asp|Asn|Lys|Ser|Asn|Phe|Tyr|Cys|Leu|Cys|Asn|
| | | | |85| | | | |90| | | | |95| |

| | | | | | | | | | | | | | | | |
|---|---|---|---|---|---|---|---|---|---|---|---|---|---|---|---|
|Arg|Gly|Tyr|Ile|Gln|Tyr|Glu|Asp|Lys|Cys|Ile|Gln|Ala|Glu|Cys|Asn|
| | | |100| | | | |105| | | | |110| | |

| | | | | | | | | | | | | | | | |
|---|---|---|---|---|---|---|---|---|---|---|---|---|---|---|---|
|Tyr|Lys|Glu|Cys|Gly|Glu|Gly|Lys|Cys|Val|Trp|Asp|Gly|Ile|His|Glu|
| | |115| | | | |120| | | | |125| | | |

| | | | | | | | | | | | | | | |
|---|---|---|---|---|---|---|---|---|---|---|---|---|---|---|
| Asp | Gly | Ala | Phe | Cys | Ser | Cys | Asn | Ile | Gly | Lys | Val | Ile | Asn | Pro | Glu |
| | 130 | | | | 135 | | | | | 140 | | | | |
| Asp | Asn | Asn | Lys | Cys | Thr | Lys | Asp | Gly | Asp | Thr | Lys | Cys | Thr | Leu | Glu |
| 145 | | | | | 150 | | | | | 155 | | | | | 160 |
| Cys | Ala | Gln | Gly | Lys | Lys | Cys | Ile | Lys | His | Asp | Val | Tyr | Tyr | Met | Cys |
| | | | | 165 | | | | | 170 | | | | | 175 | |
| Gly | Asn | Asp | Asn | Ser | Gly | Ser | Gly | Ser | Gly | Gly | Gly | Gly | Gly | Gly | Gly |
| | | | | 180 | | | | | 185 | | | | | 190 | |
| Asn | Ser | Pro | Pro | Pro | Ser | Ser | Gly | Asn | Ser | Thr | Leu | Ser | Leu | Phe | Asn |
| | | | 195 | | | | | 200 | | | | | 205 | | |
| Ala | Leu | Asn | Ile | Val | Phe | Leu | Ile | Ala | Val | Ile | Tyr | Ile | Ile | | |
| | | 210 | | | | | 215 | | | | 220 | | | | |

(2) INFORMATION FOR SEQ ID NO:3:

(i) SEQUENCE CHARACTERISTICS:
        (A) LENGTH: 804 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 60..716
        (D) OTHER INFORMATION: /product="Pfs28 surface protein
        from Plasmodium falciparum"

(xi) SEQUENCE DESCRIPTION: SEQ ID NO:3:

```
ATAGATATGT ACATTATTAA TAATCACTTA TTATTTTATA TTTTTTAGTT TTTTATACA          59
```

| | | | | | | | | | | | | | | | | |
|---|---|---|---|---|---|---|---|---|---|---|---|---|---|---|---|---|
| ATG | AAT | ACA | TAT | TTT | AAG | GTA | CTT | CTT | TTT | TTA | TTT | ATT | CAA | CTT | TAC | 107 |
| Met | Asn | Thr | Tyr | Phe | Lys | Val | Leu | Leu | Phe | Leu | Phe | Ile | Gln | Leu | Tyr | |
| 1 | | | | 5 | | | | | 10 | | | | | 15 | | |
| ATA | ACG | TTG | AAT | AAG | GCT | CGG | GTT | ACT | GAA | AAT | ACA | ATA | TGT | AAA | TAT | 155 |
| Ile | Thr | Leu | Asn | Lys | Ala | Arg | Val | Thr | Glu | Asn | Thr | Ile | Cys | Lys | Tyr | |
| | | | 20 | | | | | 25 | | | | | 30 | | | |
| GGT | TAT | TTA | ATT | CAG | ATG | AGT | AAT | CAT | TAT | GAA | TGT | AAG | TGT | ATT | GAA | 203 |
| Gly | Tyr | Leu | Ile | Gln | Met | Ser | Asn | His | Tyr | Glu | Cys | Lys | Cys | Ile | Glu | |
| | | 35 | | | | | 40 | | | | | 45 | | | | |
| GGA | TAT | GTA | TTA | ATA | AAT | GAG | GAC | ACG | TGT | GGA | AAA | AAA | GTA | GTC | TGT | 251 |
| Gly | Tyr | Val | Leu | Ile | Asn | Glu | Asp | Thr | Cys | Gly | Lys | Lys | Val | Val | Cys | |
| | 50 | | | | | 55 | | | | | 60 | | | | | |
| GAT | AAA | GTT | GAA | AAT | TCA | TTT | AAA | GCT | TGT | GAT | GAA | TAC | GCT | TAC | TGT | 299 |
| Asp | Lys | Val | Glu | Asn | Ser | Phe | Lys | Ala | Cys | Asp | Glu | Tyr | Ala | Tyr | Cys | |
| 65 | | | | | 70 | | | | | 75 | | | | | 80 | |
| TTC | GAT | TTA | GGA | AAT | AAG | AAT | AAT | GAA | AAA | CAG | ATA | AAA | TGT | ATG | TGC | 347 |
| Phe | Asp | Leu | Gly | Asn | Lys | Asn | Asn | Glu | Lys | Gln | Ile | Lys | Cys | Met | Cys | |
| | | | | 85 | | | | | 90 | | | | | 95 | | |
| AGA | ACA | GAA | TAT | ACT | TTA | ACT | GCT | GGA | GTA | TGT | GTT | CCT | AAT | GTT | TGT | 395 |
| Arg | Thr | Glu | Tyr | Thr | Leu | Thr | Ala | Gly | Val | Cys | Val | Pro | Asn | Val | Cys | |
| | | | 100 | | | | | 105 | | | | | 110 | | | |
| CGA | GAT | AAA | GTA | TGT | GGT | AAA | GGA | AAA | TGT | ATA | GTA | GAT | CCT | GCA | AAT | 443 |
| Arg | Asp | Lys | Val | Cys | Gly | Lys | Gly | Lys | Cys | Ile | Val | Asp | Pro | Ala | Asn | |
| | | | 115 | | | | | 120 | | | | | 125 | | | |
| TCT | TTA | ACA | CAT | ACA | TGC | TCA | TGC | AAT | ATA | GGT | ACC | ATA | CTT | AAC | CAG | 491 |
| Ser | Leu | Thr | His | Thr | Cys | Ser | Cys | Asn | Ile | Gly | Thr | Ile | Leu | Asn | Gln | |
| | | 130 | | | | | 135 | | | | | 140 | | | | |
| AAT | AAA | TTA | TGT | GAT | ATA | CAA | GGT | GAT | ACA | CCA | TGT | TCA | TTA | AAA | TGT | 539 |
| Asn | Lys | Leu | Cys | Asp | Ile | Gln | Gly | Asp | Thr | Pro | Cys | Ser | Leu | Lys | Cys | |
| 145 | | | | | 150 | | | | | 155 | | | | | 160 | |
| GCA | GAA | AAT | GAA | GTG | TGT | ACA | TTA | GAA | GGA | AAT | TAT | TAT | ACA | TGT | AAA | 587 |

| | | | | | | | | | | | | | | |
|---|---|---|---|---|---|---|---|---|---|---|---|---|---|---|
| Ala | Glu | Asn | Glu | Val | Cys | Thr | Leu | Glu | Gly | Asn | Tyr | Tyr | Thr | Cys Lys |
| | | | 165 | | | | | 170 | | | | | 175 | |

```
GAA GAT CCT TCA TCT AAC GGA GGA GGA AAT ACT GTG GAC CAG GCT GAT       635
Glu Asp Pro Ser Ser Asn Gly Gly Gly Asn Thr Val Asp Gln Ala Asp
            180                 185                 190

ACA TCA TAT AGT GTA ATA AAC GGA GTA ACC CTA ACA CAC GTT CTG ATT       683
Thr Ser Tyr Ser Val Ile Asn Gly Val Thr Leu Thr His Val Leu Ile
            195                 200                 205

GTA TGC TCA ATA TTT ATT AAA TTG TTA ATA TAAAAAAAAA ATATATATAT         733
Val Cys Ser Ile Phe Ile Lys Leu Leu Ile
            210                 215

ATGTATATAT ATATATATAT ATATATATAT ATATATATAT ATATATATGT CATATGATTT     793

GCATCTTATT T                                                          804
```

( 2 ) INFORMATION FOR SEQ ID NO:4:

( i ) SEQUENCE CHARACTERISTICS:
          ( A ) LENGTH: 218 amino acids
          ( B ) TYPE: amino acid
          ( D ) TOPOLOGY: linear ( i i ) MOLECULE TYPE: protein ( x i ) SEQUENCE DESCRIPTION: SEQ ID NO:4:

```
Met Asn Thr Tyr Phe Lys Val Leu Leu Phe Leu Phe Ile Gln Leu Tyr
  1               5                  10                  15

Ile Thr Leu Asn Lys Ala Arg Val Thr Glu Asn Thr Ile Cys Lys Tyr
             20                  25                  30

Gly Tyr Leu Ile Gln Met Ser Asn His Tyr Glu Cys Lys Cys Ile Glu
             35                  40                  45

Gly Tyr Val Leu Ile Asn Glu Asp Thr Cys Gly Lys Lys Val Val Cys
             50                  55                  60

Asp Lys Val Glu Asn Ser Phe Lys Ala Cys Asp Glu Tyr Ala Tyr Cys
 65                  70                  75                  80

Phe Asp Leu Gly Asn Lys Asn Asn Glu Lys Gln Ile Lys Cys Met Cys
             85                  90                  95

Arg Thr Glu Tyr Thr Leu Thr Ala Gly Val Cys Val Pro Asn Val Cys
            100                 105                 110

Arg Asp Lys Val Cys Gly Lys Gly Lys Cys Ile Val Asp Pro Ala Asn
            115                 120                 125

Ser Leu Thr His Thr Cys Ser Cys Asn Ile Gly Thr Ile Leu Asn Gln
            130                 135                 140

Asn Lys Leu Cys Asp Ile Gln Gly Asp Thr Pro Cys Ser Leu Lys Cys
145                 150                 155                 160

Ala Glu Asn Glu Val Cys Thr Leu Glu Gly Asn Tyr Tyr Thr Cys Lys
            165                 170                 175

Glu Asp Pro Ser Ser Asn Gly Gly Gly Asn Thr Val Asp Gln Ala Asp
            180                 185                 190

Thr Ser Tyr Ser Val Ile Asn Gly Val Thr Leu Thr His Val Leu Ile
            195                 200                 205

Val Cys Ser Ile Phe Ile Lys Leu Leu Ile
            210                 215
```

( 2 ) INFORMATION FOR SEQ ID NO:5:

( i ) SEQUENCE CHARACTERISTICS:
          ( A ) LENGTH: 23 base pairs
          ( B ) TYPE: nucleic acid
          ( C ) STRANDEDNESS: single (D) TOPOLOGY: linear (ii) MOLECULE TYPE: DNA (ix) FEATURE:
(A) NAME/KEY: -
(B) LOCATION: 1..23
(D) OTHER INFORMATION: /note="probe NT14AGT"

(xi) SEQUENCE DESCRIPTION: SEQ ID NO:5:

TTRTTRTCYT TGTATGGRTC YTC    23

(2) INFORMATION FOR SEQ ID NO:6:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1..20
(D) OTHER INFORMATION: /note="PfPCR28S1 primer"

(xi) SEQUENCE DESCRIPTION: SEQ ID NO:6:

GGWTWTYTAA TWSAGATGAG    20

(2) INFORMATION FOR SEQ ID NO:7:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1..22
(D) OTHER INFORMATION: /note="PfPCR28A1 primer"

(xi) SEQUENCE DESCRIPTION: SEQ ID NO:7:

ACTWTRCCWA TAWACATGAR CA    22

(2) INFORMATION FOR SEQ ID NO:8:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1..35
(D) OTHER INFORMATION: /note="Pfs28SL primer"

(xi) SEQUENCE DESCRIPTION: SEQ ID NO:8:

GCTTGTGATG AATACGCTTA CTGTTTCGAT TTAGG    35

(2) INFORMATION FOR SEQ ID NO:9:

(i) SEQUENCE CHARACTERISTICS:
(A) LENGTH: 18 base pairs
(B) TYPE: nucleic acid
(C) STRANDEDNESS: single (D) TOPOLOGY: linear (ii) MOLECULE TYPE: DNA (ix) FEATURE:
        (A) NAME/KEY: -
        (B) LOCATION: 1..18
        (D) OTHER INFORMATION: /note="Pfs28S2 primer"

(xi) SEQUENCE DESCRIPTION: SEQ ID NO:9:

GAGGACACGT GTGGAAAG                                                                                18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note="Pfs28SLA1 primer"

(xi) SEQUENCE DESCRIPTION: SEQ ID NO:10:

CCATACTTAA CCACAATA                                                                                18